(12) United States Patent
Dekker (10) Patent No.: US 7,404,977 B2
(45) Date of Patent: Jul. 29, 2008

(54) RENNETS

(75) Inventor: Petrus Jacobus Theodorus Dekker, Vonkstraat (NL)

(73) Assignee: DSM IP Assets B.V., Te Heerlen (NL)

( * ) Notice: Subject to any disclaimer, the term of this patent is extended or adjusted under 35 U.S.C. 154(b) by 274 days.

(21) Appl. No.: 10/499,661

(22) PCT Filed: Dec. 19, 2002

(86) PCT No.: PCT/EP02/14821

§ 371 (c)(1), (2), (4) Date: Feb. 8, 2005

(87) PCT Pub. No.: WO03/054186

PCT Pub. Date: Jul. 3, 2003

(65) Prior Publication Data

US 2007/0104834 A1    May 10, 2007

(30) Foreign Application Priority Data

Dec. 21, 2001    (EP) .................................. 01205117

(51) Int. Cl.
- *A23C 9/12* (2006.01)
- *C12N 9/58* (2006.01)
- *C12N 1/00* (2006.01)
- *G06F 15/00* (2006.01)

(52) U.S. Cl. ...................... 426/37; 435/223; 435/254.3; 435/254.1; 712/1

(58) Field of Classification Search .................... 426/37; 435/223, 254.1, 254.3; 712/1
See application file for complete search history.

(56) References Cited

FOREIGN PATENT DOCUMENTS

| | | |
|---|---|---|
| EP | 0489718 | 6/1992 |
| WO | WO 94/25580 | 11/1994 |
| WO | WO 98/46772 | 10/1998 |
| WO | WO 99/32617 | 7/1999 |
| WO | WO 99/38956 | 8/1999 |

OTHER PUBLICATIONS

International Search Report for PCT/EP02/14821, mailed on Apr. 25, 2003, 4 pages.
Jarai et al., Gene (1994) 145(2):171-178.
Martin et al., Biochem. Biophys. Acta (1980) 612:410-420.
Minambres et al., Biochem. Biophys. Res. Commun. (2000) 272:477-479.
O'Donoghue et al., "*Talaromyces emersonii* pepsin-type protease gene, partial cds." Database EMBL 'Online,' (Dec. 13, 2001):Database accession No. AF439995 XP002213596.
Shakeel-Ur-Rehman et al., Lait (1998):607-620.
Takeuchi et al., Advances in Experimental Medicine and Biology (1995) 362:577-580.
Thompson et al., Nucleic Acid Res. (1994) 22:4673-4680.
Tung et al., "PCR Amplification of Specific Sequences from a cDNA Library," PCR Technology, Erlich, (ed.), (1989) pp. 99-104.

*Primary Examiner*—Tekchand Saidha
*Assistant Examiner*—Malgorzata A. Walicka
(74) *Attorney, Agent, or Firm*—Nixon & Vanderhye PC (57) ABSTRACT

The present invention describes an aspartic protease produced by a fungus from the class Eurotiomycetes, comprising the amino acid sequence of FDTGSSD or FDTGSSE. The present invention further provides a process for identifying new milk clotting enzymes comprising screening an amino acid sequence for the presence of FDTGSSD or FDTGSSE. The enzymes of the invention may he useful in cheese production.

6 Claims, 2 Drawing Sheets

SEQUENCE LISTING

<160> NUMBER OF SEQ ID NOS: 19

<210> SEQ ID NO 1
<211> LENGTH: 2044
<212> TYPE: DNA
<213> ORGANISM: Aspergillus niger

<400> SEQUENCE: 1

```
ggctttgttg ggctgagcgc tacttctttc tctctcttgg tctgttcgtt gctccgccag      60
ttggttcact cagcctcgta acatcagtat accaggctaa gtcaggactt tggcccccat     120
actgcttccc cttttttat aaaactcaat ccttctggaa aggattctat ttctcaattc      180
tcagactact taatacgttc tttgttttca aattgttttg tttctgaaac ttgccgggcc     240
ctatcccctc ttttttatag tccgcctgtc gacatcatat ccagagtgag ccaccatgca     300
gctcctccag tccctcattg ttgccgtttg cttcagctac ggcgtcctct ccttacccca     360
tggcccgtca aaccagcaca aagcacgttc cttcaaggtt gaacgggtcc gtcgtggaac     420
cggtgctctg catgggcccg ctgctctccg caaagcatac cggaagtacg gaatagctcc     480
cagcagtttc aacatcgatc tggcagactt taaacccatt acgacaaccc atgctgctgc     540
tgggagcgag attgcagagc ctgatcagac tggcgctgtc agtgctactt ccgtcgagaa     600
cgatgccgag ttcgtttcgc ctgttcttat tggcggccag aagatcgtca tgacatttga     660
cactggttct tctgacttgt aagtcttgga tgcagctgtt tactctttgg tacagtgatt     720
aacgtcgatc tacagttggg tgttcgatac gaatctcaat gaaaccttga cgggacacac     780
ggagtacaac ccttcgaact cctcgacctt caagaagatg gacggataca ccttcgatgt     840
ctcgtatggt gacgactcgt acgcctctgg ccccgtcgga acggataccg tcaacattgg     900
cggcgccatt gtcaaggagc aagccttcgg tgtccccgac caggtatccc agtcgttcat     960
cgaggacacg aactccaacg gcctggtcgg gttgggcttt tcctccatca acaccatcaa    1020
accggaggcg caagacacgt tcttcgccaa tgtcgcacca agtctggacg agcccgtcat    1080
gaccgcctcg ctcaaggctg acggagtggg cgagtacgag ttcggcacga tcgacaaaga    1140
caagtaccag ggcaacattg ccaacatcag cgtggactca tcgaacggat actggcagtt    1200
ctccactccc aagtactccg tggcagacgg agagctgaag gacattggaa gcttgaacac    1260
ctcgatcgcg gacaccggta cctccctat gctgctggat gaagacgtgg ttactgccta    1320
ctatgcgcaa gttcccaact cggtctacgt gagcagtgcc ggtggttaca tctacccctg    1380
caacaccact cttcccagct tctcgcttgt cctcggcgag tcgagcctgg ccacgatccc    1440
cggtaacctg atcaatttct ccaaggttgg caccaacacc accaccggac aggcctgtaa    1500
gttgctcccc ttcttttgca tgattgaaca tgattgactg attgtgctgg ttagtgtgct    1560
ttggcggcat tcaatccaac ggaaacacct cgctgcagat tctgggcgat atttccctga    1620
aggccttttt cgttgtcttc gacatgcgcg gccccctcgct tggtgttgcc ctcccaaga    1680
actagtttcc ttttcctgta cttttccccc gcgtgtaata atatcgtctg attttttgga    1740
ctgtctccta cgtgggcaag atggatggat agtttgctca cgtgcattgc tttaccttgg    1800
gtctgtgagt caaggcagga gtgcgtggct gtatctacaa ttcaagttac agtgccgacc    1860
```

-continued

```
gttattgcct tccacatcga aaaacataga cactctttct aaccctaatc catgatacaa    1920
gtatatactt cgagtccata ttatggtggt gtatcaaggc gccatgttta tatctaatga    1980
aaccaacgta ggtctcatct tcatacgttg tttaaaaggt gccgaagaat atacgaagat    2040
agat                                                                 2044
```

<210> SEQ ID NO 2
<211> LENGTH: 1275
<212> TYPE: DNA
<213> ORGANISM: Aspergillus niger

<400> SEQUENCE: 2

```
atgcagctcc tccagtccct cattgttgcc gtttgcttca gctacggcgt cctctcctta     60
ccccatggcc cgtcaaacca gcacaaagca cgttccttca aggttgaacg ggtccgtcgt    120
ggaaccggtg ctctgcatgg gcccgctgct ctccgcaaag cataccggaa gtacggaata    180
gctcccagca gtttcaacat cgatctggca gactttaaac ccattacgac aacccatgct    240
gctgctggga gcgagattgc agagcctgat cagactggcg ctgtcagtgc tacttccgtc    300
gagaacgatg ccgagttcgt ttcgcctgtt cttattggcg ccagaagat cgtcatgaca    360 tttgacactg gttcttctga cttttgggtg ttcgatacga atctcaatga aaccttgacg    420
ggacacacgt agtacaaccc ttcgaactcc tcgaccttca agaagatgga cggatacacc    480
ttcgatgtct cgtatggtga cgactcgtac gcctctggcc ccgtcggaac ggataccgtc    540
aacattggcg cgccattgt caaggagcaa gccttcggtg tccccgacca ggtatcccag    600
tcgttcatcg aggacacgaa ctccaacggc ctggtcgggt gggcttttc ctccatcaac    660 accatcaaac cggaggcgca agacacgttc ttcgccaatg tcgcaccaag tctggacgag    720
cccgtcatga ccgcctcgct caaggctgac ggagtgggcg agtacgagtt cggcacgatc    780
gacaaagaca gtaccaggg caacattgcc aacatcagcg tggactcatc gaacggatac    840
tggcagttct ccactcccaa gtactccgtg gcagacggag agctgaagga cattggaagc    900
ttgaacacct cgatcgcgga caccggtacc tcccttatgc tgctggatga agacgtggtt    960
actgcctact atgcgcaagt tcccaactcg gtctacgtga gcagtgccgg tggttacatc   1020
tacccctgca caccactct tcccagcttc tcgcttgtcc tcggcgagtc gagcctggcc   1080
acgatccccg gtaacctgat caatttctcc aaggttggca ccaacaccac caccggacag   1140
gccttgtgct ttggcggcat tcaatccaac ggaaacacct cgctgcagat tctgggcgat   1200
attttcctga aggcctttt cgttgtcttc gacatgcgcg cccctcgct tggtgttgcc   1260 tctcccaaga actag                                                    1275
```

<210> SEQ ID NO 3
<211> LENGTH: 424
<212> TYPE: PRT
<213> ORGANISM: Aspergillus niger

<400> SEQUENCE: 3

```
Met Gln Leu Leu Gln Ser Leu Ile Val Ala Val Cys Phe Ser Tyr Gly
1               5                   10                  15

Val Leu Ser Leu Pro His Gly Pro Ser Asn Gln His Lys Ala Arg Ser
            20                  25                  30

Phe Lys Val Glu Arg Val Arg Arg Gly Thr Gly Ala Leu His Gly Pro
        35                  40                  45

Ala Ala Leu Arg Lys Ala Tyr Arg Lys Tyr Gly Ile Ala Pro Ser Ser
    50                  55                  60
```

```
Phe Asn Ile Asp Leu Ala Asp Phe Lys Pro Ile Thr Thr Thr His Ala
 65                  70                  75                  80

Ala Ala Gly Ser Glu Ile Ala Glu Pro Asp Gln Thr Gly Ala Val Ser
                 85                  90                  95

Ala Thr Ser Val Glu Asn Asp Ala Glu Phe Val Ser Pro Val Leu Ile
                100                 105                 110

Gly Gly Gln Lys Ile Val Met Thr Phe Asp Thr Gly Ser Ser Asp Phe
                115                 120                 125

Trp Val Phe Asp Thr Asn Leu Asn Glu Thr Leu Thr Gly His Thr Glu
            130                 135                 140

Tyr Asn Pro Ser Asn Ser Ser Thr Phe Lys Lys Met Asp Gly Tyr Thr
145                 150                 155                 160

Phe Asp Val Ser Tyr Gly Asp Asp Ser Tyr Ala Ser Gly Pro Val Gly
                165                 170                 175

Thr Asp Thr Val Asn Ile Gly Gly Ala Ile Val Lys Glu Gln Ala Phe
                180                 185                 190

Gly Val Pro Asp Gln Val Ser Gln Ser Phe Ile Glu Asp Thr Asn Ser
            195                 200                 205

Asn Gly Leu Val Gly Leu Gly Phe Ser Ser Ile Asn Thr Ile Lys Pro
210                 215                 220

Glu Ala Gln Asp Thr Phe Phe Ala Asn Val Ala Pro Ser Leu Asp Glu
225                 230                 235                 240

Pro Val Met Thr Ala Ser Leu Lys Ala Asp Gly Val Gly Glu Tyr Glu
                245                 250                 255

Phe Gly Thr Ile Asp Lys Asp Lys Tyr Gln Gly Asn Ile Ala Asn Ile
                260                 265                 270

Ser Val Asp Ser Ser Asn Gly Tyr Trp Gln Phe Ser Thr Pro Lys Tyr
            275                 280                 285

Ser Val Ala Asp Gly Glu Leu Lys Asp Ile Gly Ser Leu Asn Thr Ser
290                 295                 300

Ile Ala Asp Thr Gly Thr Ser Leu Met Leu Leu Asp Glu Asp Val Val
305                 310                 315                 320

Thr Ala Tyr Tyr Ala Gln Val Pro Asn Ser Val Tyr Val Ser Ser Ala
                325                 330                 335

Gly Gly Tyr Ile Tyr Pro Cys Asn Thr Thr Leu Pro Ser Phe Ser Leu
                340                 345                 350

Val Leu Gly Glu Ser Ser Leu Ala Thr Ile Pro Gly Asn Leu Ile Asn
            355                 360                 365

Phe Ser Lys Val Gly Thr Asn Thr Thr Thr Gly Gln Ala Leu Cys Phe
370                 375                 380

Gly Gly Ile Gln Ser Asn Gly Asn Thr Ser Leu Gln Ile Leu Gly Asp
385                 390                 395                 400

Ile Phe Leu Lys Ala Phe Phe Val Phe Asp Met Arg Gly Pro Ser
                405                 410                 415

Leu Gly Val Ala Ser Pro Lys Asn
            420

<210> SEQ ID NO 4
<211> LENGTH: 7
<212> TYPE: PRT
<213> ORGANISM: Artificial Sequence
<220> FEATURE:
<223> OTHER INFORMATION: consensus amino acid sequence for coagulants

<400> SEQUENCE: 4
```

Phe Asp Thr Gly Ser Ser Asp
1               5

<210> SEQ ID NO 5
<211> LENGTH: 7
<212> TYPE: PRT
<213> ORGANISM: Artificial Sequence
<220> FEATURE:
<223> OTHER INFORMATION: consensus amino acid sequence for coagulants

<400> SEQUENCE: 5

Phe Asp Thr Gly Ser Ser Glu
1               5

<210> SEQ ID NO 6
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 9, 12, 15, and 18 is any of g,
      a, t or c

<400> SEQUENCE: 6
ttygayacng gntcntcnga                                          20

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: N at positions 9, 12 and 15 is any of g, a, t
      or c
<220> FEATURE:
<223> OTHER INFORMATION: degenerate oligonucleotide

<400> SEQUENCE: 7
ttygayacng gntcnagyga                                          20

<210> SEQ ID NO 8
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 9, 12 and 18 is any of g, a, t
      or c

<400> SEQUENCE: 8
ttygayacng gnagytcnga                                          20

<210> SEQ ID NO 9
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 9 and 12 is any of g, a, t or c

<400> SEQUENCE: 9
ttygayacng gnagyagyga                                          20

<210> SEQ ID NO 10
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 3, 6, 9 and 12 is any of g, a,
      t or c

<400> SEQUENCE: 10
tcnganganc cngtrtcraa                                          20

<210> SEQ ID NO 11
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 6, 9 and 12 is any of g, a,
      t or c

<400> SEQUENCE: 11
tcrctnganc cngtrtcraa                                          20

<210> SEQ ID NO 12
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 3, 9 and 12 is any of g, a,
      t or c

<400> SEQUENCE: 12
tcngarctnc cngtrtcraa                                          20

<210> SEQ ID NO 13
<211> LENGTH: 20
<212> TYPE: DNA
<213> ORGANISM: Artificial Sequence
<220> FEATURE:
<223> OTHER INFORMATION: degenerate oligonucleotide
<220> FEATURE:
<221> NAME/KEY: misc_feature
<222> LOCATION: (1)..(20)
<223> OTHER INFORMATION: N at positions 9 and 12 is any of g, a, t or c

<400> SEQUENCE: 13
tcrctrctnc cngtrtcraa                                          20

<210> SEQ ID NO 14
<211> LENGTH: 430
<212> TYPE: PRT
<213> ORGANISM: Rhizomucor miehei

<400> SEQUENCE: 14

```
Met Leu Phe Ser Gln Ile Thr Ser Ala Ile Leu Leu Thr Ala Ala Ser
1               5                   10                  15

Leu Ser Leu Thr Thr Ala Arg Pro Val Ser Lys Gln Ser Glu Ser Lys
            20                  25                  30

Asp Lys Leu Ala Leu Pro Leu Thr Ser Val Ser Arg Lys Phe Ser
            35                  40                  45

Gln Thr Lys Phe Gly Gln Gln Leu Ala Glu Lys Leu Ala Gly Leu
50                      55                  60

Lys Pro Phe Ser Glu Ala Ala Asp Gly Ser Val Asp Thr Pro Gly
65              70                  75                  80

Tyr Tyr Asp Phe Asp Leu Glu Glu Tyr Ala Ile Pro Val Ser Ile Gly
                85                  90                  95

Thr Pro Gly Gln Asp Phe Leu Leu Phe Asp Thr Gly Ser Ser Asp
            100                 105                 110

Thr Trp Val Pro His Lys Gly Cys Thr Lys Ser Glu Gly Cys Val Gly
            115                 120                 125

Ser Arg Phe Phe Asp Pro Ser Ala Ser Ser Thr Phe Lys Ala Thr Asn
130                 135                 140

Tyr Asn Leu Asn Ile Thr Tyr Gly Thr Gly Gly Ala Asn Gly Leu Tyr
145                 150                 155                 160

Phe Glu Asp Ser Ile Ala Ile Gly Asp Ile Thr Val Thr Lys Gln Ile
                165                 170                 175

Leu Ala Tyr Val Asp Asn Val Arg Gly Pro Thr Ala Glu Gln Ser Pro
            180                 185                 190

Asn Ala Asp Ile Phe Leu Asp Gly Leu Phe Gly Ala Ala Tyr Pro Asp
            195                 200                 205

Asn Thr Ala Met Glu Ala Glu Tyr Gly Ser Thr Tyr Asn Thr Val His
            210                 215                 220

Val Asn Leu Tyr Lys Gln Gly Leu Ile Ser Ser Pro Leu Phe Ser Val
225                 230                 235                 240

Tyr Met Asn Thr Asn Ser Gly Thr Gly Glu Val Val Phe Gly Gly Val
                245                 250                 255

Asn Asn Thr Leu Leu Gly Gly Asp Ile Ala Tyr Thr Asp Val Met Ser
            260                 265                 270

Arg Tyr Gly Gly Tyr Tyr Phe Trp Asp Ala Pro Val Thr Gly Ile Thr
            275                 280                 285

Val Asp Gly Ser Ala Ala Val Arg Phe Ser Arg Pro Gln Ala Phe Thr
            290                 295                 300

Ile Asp Thr Gly Thr Asn Phe Phe Ile Met Pro Ser Ala Ala Ser
305                 310                 315                 320

Lys Ile Val Lys Ala Ala Leu Pro Asp Ala Thr Glu Thr Gln Gln Gly
                325                 330                 335

Trp Val Val Pro Cys Ala Ser Tyr Gln Asn Ser Lys Ser Thr Ile Ser
            340                 345                 350

Ile Val Met Gln Lys Ser Gly Ser Ser Asp Thr Ile Glu Ile Ser
            355                 360                 365

Val Pro Val Ser Lys Met Leu Leu Pro Val Asp Gln Ser Asn Glu Thr
            370                 375                 380

Cys Met Phe Ile Ile Leu Pro Asp Gly Gly Asn Gln Tyr Ile Val Gly
385                 390                 395                 400

Asn Leu Phe Leu Arg Phe Phe Val Asn Val Tyr Asp Phe Gly Asn Asn
                405                 410                 415
```

-continued

Arg Ile Gly Phe Ala Pro Leu Ala Ser Ala Tyr Glu Asn Glu
            420             425             430

<210> SEQ ID NO 15
<211> LENGTH: 427
<212> TYPE: PRT
<213> ORGANISM: Rhizomucor pusillus

<400> SEQUENCE: 15

Met Leu Phe Ser Lys Ile Ser Ser Ala Ile Leu Leu Thr Ala Ala Ser
1               5                   10                  15

Phe Ala Leu Thr Ser Ala Arg Pro Val Ser Lys Gln Ser Asp Ala Asp
            20                  25                  30

Asp Lys Leu Leu Ala Leu Pro Leu Thr Ser Val Asn Arg Lys Tyr Ser
        35                  40                  45

Gln Thr Lys His Gly Gln Gln Ala Ala Glu Lys Leu Gly Gly Ile Lys
    50                  55                  60

Ala Phe Ala Glu Gly Asp Gly Ser Val Asp Thr Pro Gly Leu Tyr Asp
65                  70                  75                  80

Phe Asp Leu Glu Glu Tyr Ala Ile Pro Val Ser Ile Gly Thr Pro Gly
                85                  90                  95

Gln Asp Phe Tyr Leu Leu Phe Asp Thr Gly Ser Ser Asp Thr Trp Val
            100                 105                 110

Pro His Lys Gly Cys Asp Asn Ser Glu Gly Cys Val Gly Lys Arg Phe
        115                 120                 125

Phe Asp Pro Ser Ser Ser Thr Phe Lys Glu Thr Asp Tyr Asn Leu
130                 135                 140

Asn Ile Thr Tyr Gly Thr Gly Gly Ala Asn Gly Ile Tyr Phe Arg Asp
145                 150                 155                 160

Ser Ile Thr Val Gly Gly Ala Thr Val Lys Gln Gln Thr Leu Ala Tyr
                165                 170                 175

Val Asp Asn Val Ser Gly Pro Thr Ala Glu Gln Ser Pro Asp Ser Glu
            180                 185                 190

Leu Phe Leu Asp Gly Met Phe Gly Ala Ala Tyr Pro Asp Asn Thr Ala
        195                 200                 205

Met Glu Ala Glu Tyr Gly Asp Thr Tyr Asn Thr Val His Val Asn Leu
    210                 215                 220

Tyr Lys Gln Gly Leu Ile Ser Ser Pro Val Phe Ser Val Tyr Met Asn
225                 230                 235                 240

Thr Asn Asp Gly Gly Gln Val Val Phe Gly Gly Ala Asn Asn Thr
                245                 250                 255

Leu Leu Gly Gly Asp Ile Gln Tyr Thr Asp Val Leu Lys Ser Arg Gly
            260                 265                 270

Gly Tyr Phe Phe Trp Asp Ala Pro Val Thr Gly Val Lys Ile Asp Gly
        275                 280                 285

Ala Asp Ala Val Ser Phe Asp Gly Ala Gln Ala Phe Thr Ile Asp Thr
    290                 295                 300

Gly Thr Asn Phe Phe Ile Ala Pro Ser Ser Phe Ala Glu Lys Val Val
305                 310                 315                 320

Lys Ala Ala Leu Pro Asp Ala Thr Glu Ser Gln Gln Gly Tyr Thr Val
                325                 330                 335

Pro Cys Ser Lys Tyr Gln Asp Ser Lys Thr Thr Phe Ser Leu Val Leu
            340                 345                 350

Gln Lys Ser Gly Ser Ser Asp Thr Ile Asp Val Ser Val Pro Ile
        355                 360                 365

```
Ser Lys Met Leu Leu Pro Val Asp Lys Ser Gly Glu Thr Cys Met Phe
    370                 375                 380

Ile Val Leu Pro Asp Gly Gly Asn Gln Phe Ile Val Gly Asn Leu Phe
385                 390                 395                 400

Leu Arg Phe Phe Val Asn Val Tyr Asp Phe Gly Lys Asn Arg Ile Gly
                    405                 410                 415

Phe Ala Pro Leu Ala Ser Gly Tyr Glu Asn Asn
                420                 425
```

<210> SEQ ID NO 16
<211> LENGTH: 381
<212> TYPE: PRT
<213> ORGANISM: Bos taurus

<400> SEQUENCE: 16

```
Met Arg Cys Leu Val Val Leu Leu Ala Val Phe Ala Leu Ser Gln Gly
1               5                   10                  15

Ala Glu Ile Thr Arg Ile Pro Leu Tyr Lys Gly Lys Ser Leu Arg Lys
                20                  25                  30

Ala Leu Lys Glu His Gly Leu Leu Glu Asp Phe Leu Gln Lys Gln Gln
                35                  40                  45

Tyr Gly Ile Ser Ser Lys Tyr Ser Gly Phe Gly Glu Val Ala Ser Val
    50                  55                  60

Pro Leu Thr Asn Tyr Leu Asp Ser Gln Tyr Phe Gly Lys Ile Tyr Leu
65                  70                  75                  80

Gly Thr Pro Pro Gln Glu Phe Thr Val Leu Phe Asp Thr Gly Ser Ser
                    85                  90                  95

Asp Phe Trp Val Pro Ser Ile Tyr Cys Lys Ser Asn Ala Cys Lys Asn
                100                 105                 110

His Gln Arg Phe Asp Pro Arg Lys Ser Ser Thr Phe Gln Asn Leu Gly
                115                 120                 125

Lys Pro Leu Ser Ile His Tyr Gly Thr Gly Ser Met Gln Gly Ile Leu
            130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                    165                 170                 175

Phe Asp Gly Ile Leu Gly Met Ala Tyr Pro Ser Leu Ala Ser Glu Tyr
                180                 185                 190

Ser Ile Pro Val Phe Asp Asn Met Met Asn Arg His Leu Val Ala Gln
            195                 200                 205

Asp Leu Phe Ser Val Tyr Met Asp Arg Asn Gly Gln Glu Ser Met Leu
    210                 215                 220

Thr Leu Gly Ala Ile Asp Pro Ser Tyr Tyr Thr Gly Ser Leu His Trp
225                 230                 235                 240

Val Pro Val Thr Val Gln Gln Tyr Trp Gln Phe Thr Val Asp Ser Val
                    245                 250                 255

Thr Ile Ser Gly Val Val Ala Cys Glu Gly Gly Cys Gln Ala Ile
                260                 265                 270

Leu Asp Thr Gly Thr Ser Lys Leu Val Gly Pro Ser Ser Asp Ile Leu
            275                 280                 285

Asn Ile Gln Gln Ala Ile Gly Ala Thr Gln Asn Gln Tyr Gly Glu Phe
    290                 295                 300

Asp Ile Asp Cys Asp Asn Leu Ser Tyr Met Pro Thr Val Val Phe Glu
```

```
                305                 310                 315                 320
Ile Asn Gly Lys Met Tyr Pro Leu Thr Pro Ser Ala Tyr Thr Ser Gln
                325                 330                 335

Asp Gln Gly Phe Cys Thr Ser Gly Phe Gln Ser Glu Asn His Ser Gln
            340                 345                 350

Lys Trp Ile Leu Gly Asp Val Phe Ile Arg Glu Tyr Tyr Ser Val Phe
            355                 360                 365

Asp Arg Ala Asn Asn Leu Val Gly Leu Ala Lys Ala Ile
            370                 375                 380

<210> SEQ ID NO 17
<211> LENGTH: 419
<212> TYPE: PRT
<213> ORGANISM: Cryphonectria parasitica

<400> SEQUENCE: 17

Met Ser Ser Pro Leu Lys Asn Ala Leu Val Thr Ala Met Leu Ala Gly
1               5                   10                  15

Gly Ala Leu Ser Ser Pro Thr Lys Gln His Val Gly Ile Pro Val Asn
            20                  25                  30

Ala Ser Pro Glu Val Gly Pro Gly Lys Tyr Ser Phe Lys Gln Val Arg
        35                  40                  45

Asn Pro Asn Tyr Lys Phe Asn Gly Pro Leu Ser Val Lys Lys Thr Tyr
    50                  55                  60

Leu Lys Tyr Gly Val Pro Ile Pro Ala Trp Leu Glu Asp Ala Val Gln
65                  70                  75                  80

Asn Ser Thr Ser Gly Leu Ala Glu Arg Ser Thr Gly Ser Ala Thr Thr
                85                  90                  95

Thr Pro Ile Asp Ser Leu Asp Asp Ala Tyr Ile Thr Pro Val Gln Ile
            100                 105                 110

Gly Thr Pro Ala Gln Thr Leu Asn Leu Asp Phe Asp Thr Gly Ser Ser
        115                 120                 125

Asp Leu Trp Val Phe Ser Ser Glu Thr Thr Ala Ser Glu Val Asp Gly
    130                 135                 140

Gln Thr Ile Tyr Thr Pro Ser Lys Ser Thr Thr Ala Lys Leu Leu Ser
145                 150                 155                 160

Gly Ala Thr Trp Ser Ile Ser Tyr Gly Asp Gly Ser Ser Ser Ser Gly
                165                 170                 175

Asp Val Tyr Thr Asp Thr Val Ser Val Gly Gly Leu Thr Val Thr Gly
            180                 185                 190

Gln Ala Val Glu Ser Ala Lys Lys Val Ser Ser Phe Thr Glu Asp
        195                 200                 205

Ser Thr Ile Asp Gly Leu Leu Gly Leu Ala Phe Ser Thr Leu Asn Thr
    210                 215                 220

Val Ser Pro Thr Gln Gln Lys Thr Phe Asp Asn Ala Lys Ala Ser
225                 230                 235                 240

Leu Asp Ser Pro Val Phe Thr Ala Asp Leu Gly Tyr His Ala Pro Gly
                245                 250                 255

Thr Tyr Asn Phe Gly Phe Ile Asp Thr Thr Ala Tyr Thr Gly Ser Ile
            260                 265                 270

Thr Tyr Thr Ala Val Ser Thr Lys Gln Gly Phe Trp Glu Trp Thr Ser
        275                 280                 285

Thr Gly Tyr Ala Val Gly Ser Gly Thr Phe Lys Ser Thr Ser Ile Asp
    290                 295                 300
```

```
Gly Ile Ala Asp Thr Gly Thr Thr Leu Leu Tyr Leu Pro Ala Thr Val
305                 310                 315                 320

Val Ser Ala Tyr Trp Ala Gln Val Ser Gly Ala Lys Ser Ser Ser Ser
                325                 330                 335

Val Gly Gly Tyr Val Phe Pro Cys Ser Ala Thr Leu Pro Ser Phe Thr
                340                 345                 350

Phe Gly Val Gly Ser Ala Arg Ile Val Ile Pro Gly Asp Tyr Ile Asp
            355                 360                 365

Phe Gly Pro Ile Ser Thr Gly Ser Ser Ser Cys Phe Gly Gly Ile Gln
            370                 375                 380

Ser Ser Ala Gly Ile Gly Ile Asn Ile Phe Gly Asp Val Ala Leu Lys
385                 390                 395                 400

Ala Ala Phe Val Val Phe Asn Gly Ala Thr Thr Pro Thr Leu Gly Phe
                405                 410                 415

Ala Ser Lys

<210> SEQ ID NO 18
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 18
gtactggaat tcatgcagct cctccagtcc ctc                                33

<210> SEQ ID NO 19
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 19
gtactggaat tcctagttct tgggagaggc aac                                33
```

RENNETS

CROSS-REFERENCE TO RELATED APPLICATIONS

This application is the national stage of PCT application PCT/EP02/14821 having an international filing date of 19 Dec. 2002, which claims priority from European application 01205117.3, filed 21 Dec. 2001. The contents of these documents are incorporated herein by reference.

FIELD OF THE INVENTION

The present invention relates to new milk clotting enzymes. Many proteases can be used to clot (coagulate) milk. However only very few proteases are applied in cheese making because of a low cheese yield and the unacceptable structure and taste of the resulting cheese.

Milk clotting enzymes (rennets) which are used commercially include (bovine) chymosin, *Rhizomucor miehei* protease, *Rhizomucor pusillus* protease and *Cryphonectria parasitica* protease. Chymosin can be extracted from the abomasa of suckling calves, and is subsequently purified. However the presence of pepsin in the chymosin preparation may cause more general proteolysis and loss of curd to the whey.

Chymosin can also be produced microbially by transforming microbial host cells. In this way it is possible to produce chymosin in *Escherichia coli, Saccharomyces cerevisae* or *Kluyveromyces lactis*.

*Rhizomucor miehei* protease (for example Fromase® of DSM, The Netherlands) is a good alternative for chymosin in the cheese production. This enzyme is more thermostable than chymosin, but can also be produced as a modified enzyme having about the same thermostability as chymosin.

Other milk clotting proteases also differ from chymosin in their performance during the cheese making process. For example *Rhizomucor pusillus* is more sensitive to pH changes. Other aspartic proteases, like pepsin, give a low yield or an off-tasting cheese.

Therefore there still is a need to find novel proteases produced by plants or micro organisms which would have milk clotting properties in combination with high cheese yields and a good structure and taste of the resulting cheese.

SUMMARY OF THE INVENTION

The present invention provides a method for screening for novel milk clotting enzymes. Moreover this method can be used to predict if a known protease can be used as milk-clotting enzyme.

Furthermore the present invention provides new proteases, which have this desired milk-clotting use.

The present invention provides:
(1) an aspartic protease by a fungus from the class Eurotiomycetes;
(2) a DNA sequence encoding the amino acid sequence FDTGSSD or FDTGSSE (SEQ ID NO: 4 or 5);
(3) a DNA sequence encoding an aspartic protease of (1);
(4) an expression vector comprising a DNA sequence of (3);
(5) a host cell comprising an expression vector of (4);
(6) a process for identifying new milk clotting enzymes comprising screening an amino acid sequence for the presence of FDTGSSD or FDTGSSE (SEQ ID NO: 4 or 5).

The aspartic protease comprises an amino acid sequence selected from the group of FDTGSSD and FDTGSSE (SEQ ID NO's: 4 and 5). The aspartic proteases of the invention are advantageously used in food and feed preparation, preferably in cheese production.

DETAILED DESCRIPTION

Sequence comparison of aspartic proteases, indicates that fungal coagulants have little sequence homology to chymosin. Surprisingly we have found a sequence motif that specifically recognizes genes encoding milk-clotting enzymes but is absent in other (aspartic) proteases. Using this sequence motif we were able to identify new milk-clotting enzymes from databases of protein- and/or DNA-sequences.

We have compared the amino acid sequence of different commercial milk coagulants that can be used to make cheese, with other aspartic proteases, like pepsins, that are poor in the cheese making process. This approach resulted in the identification of amino acid residues within the coagulants that might be important for obtaining good cheese quality.

A comparison of the amino acid sequence of four different milk coagulants was performed using the program Clustal W (ref Thompson J. D., Higgins D. G. and Gibson T. J. (1994) Nucleic Acid Res. 22.4673-4680). Sequences used in the alignment came from:

1. aspartic protease of *Rhizomucor miehei* (mucoropepsin). Swissprot:P00799
2. aspartic protease of *Rhizomucor pusillus* (mucoropepsin). Swissprot:P09177
3. bovine chymosin. Swissprot:P00794
4. aspartic protease of *Cryphonectria parasitica* (endothiapepsin). Swissprot:P11838

This multiple sequence alignment shows that from all amino acids in the mucoropepsin identified by SEQ ID NO's: 14-17, only 42 amino acids are conserved among all four proteins (see asterisks in Table 1). Most conservation is seen around the two catalytic aspartate residues (highlighted in dark in Table 1). The two mucoropepsins from *R. miehei* and *R. pusillus* are much more conserved. Chymosin is much more related to pepsins and cathepsins than to the fungal aspartic proteases.

TABLE 1

Amino acid sequence comparison of four coagulants using the Clustal W method. Proteins are numbered as indicated in the text. Identical residues are indicated with an asterisk, homologous residues with double or single points. Catalytic Aspartic residues are highlighted in dark. Residues that are not conserved in pepsins, gastricsin and cathepsin, but are conserved in the coagulants, are highlighted in grey.

```
1swissprot_carp_rhimi    ------------MLFSQITSAILLTAASLSLTTARPVSKQSESKDKLLAL
2swissprot_carp_rhipu    ------------MLFSKISSAILLTAASFALTSARPVSKQSDADDKLLAL
3swissprot_chym_bovin    -------------------------MRCLVVLLAVFALSQGTEITRIP
4swissprot_carp_crypa    MSSPLKNALVTAMLAGGALSSPTKQHVGIPVNASPEVGPGKYSFKQVRNP
                                                    :    *   .  . .
```

TABLE 1-continued

Amino acid sequence comparison of four coagulants using the Clustal
W method. Proteins are numbered as indicated in the text. Identical residues
are indicated with an asterisk, homologous residues with double or single points.
Catalytic Aspartic residues are highlighted in dark. Residues that are not conserved
in pepsins, gastricsin and cathepsin, but are conserved in the coagulants, are
highlighted in grey.

```
1swissprot_carp_rhimi     PLTS---VSRKFSQTKFGQQQLAEKLAGLKPFSEAAADGSVDTPGYY--D
2swissprot_carp_rhipu     PLTS---VNRKYSQTKHG-QQAAEKLGGIKAFAE--GDGSVDTPGLY--D
3swissprot_chym_bovin     LYKG---KSLRKALKEHGLLEDFLQKQQYGISSKYSGFGEVASVPLT--N
4swissprot_carp_crypa     NYKFNGPLSVKKTYLKYGVPIPAWLEDAVQNSTSGLAERSTGSATTTPID
                              .      .  :  :  : . *              :.    ...:      :

1swissprot_carp_rhimi     FDLEEYAIPVSIGTPGQDFLLLFDTGSSDTWVPHKGCTKSEGCVGSRFFD
2swissprot_carp_rhipu     FDLEEYAIPVSIGTPGQDFYLLFDTGSSDTWVPHKGCDNSEGCVGKRFFD
3swissprot_chym_bovin     YLDSQYFGKIYLGTPPQEFTVLFDTGSSDFWVPSIYC-KSNACKNHQRFD
4swissprot_carp_crypa     SLDDQYITPVQIGTPAQTLNLDFDTGSSDLWVFSSETTASEVDGQTIYTP
                             . *      :   :*** *  : :   ******  **        *:

1swissprot_carp_rhimi     PSASSTFKATNYNLNITYGTG-GANGLYFEDSIAIGDITVTKQILAYVDN
2swissprot_carp_rhipu     PSSSSTFKETDYNLNITYGTG-GANGIYFRDSITVGGATVKQQTLAYVDN
3swissprot_chym_bovin     PRKSSTFQNLGKPLSIHYGTG-SMQGILGYDTVTVSNIVDIQQTVGLSTQ
4swissprot_carp_crypa     SKSTTAKLLSGATWSISYGDGSSSSGDVYTDTVSVGGLTVTGQAVESAKK
                             .  :::    .  .* *** . .*    *:::::. .   *  :     :

1swissprot_carp_rhimi     VRGPTAEQSPNADIFLDGLFGAAYPDNTAMEAEYGSTYNTVHVNLYKQGL
2swissprot_carp_rhipu     VSGPTAEQSPDSELFLDGMFGAAYPDNTAMEAEYGDTYNTVHVNLYKQGL
3swissprot_chym_bovin     EPGDVFTYA-E--F--DGILGMAYPS---LASEYS---IPVFDNMMNRHL
4swissprot_carp_crypa     VSSSFTEDSTI-----DGLLGLAFST---LNTVSPTQQKTFFDNAKAS--
                             .      :            **::* *:.     : :        ... *

1swissprot_carp_rhimi     ISSPLFSVYMNTNSGTGEVVFGGVNNTLLGGDIAYTDVMSRYGGYYFWDA
2swissprot_carp_rhipu     ISSPVFSVYMNTNDGGGQVVFGGANNTLLGGDIQYTDVLKSRGGYFFWDA
3swissprot_chym_bovin     VAQDLFSVYMDRNGQESMLTLGAIDPSYYTGSLHWVPVTVQQ----YWQF
4swissprot_carp_crypa     LDSPVFTADLGYHAP-GTYNFGFIDTTAYTGSITYTAVSTKQG---FWEW
                             :  . :*:.  :. :   .     :*  : :    *.:  :.  *         :*:

1swissprot_carp_rhimi     PVTGITVDGSAAVRFSRPQAFTIDTGTNFFIMPSSAASKIVKAALPDATE
2swissprot_carp_rhipu     PVTGVKIDGADAVSFDGAQAFTIDTGTNFFIAPSSFAEKVVKAALPDATE
3swissprot_chym_bovin     TVDSVTISG-VVVACEGGCQAILDTGTSKLVGPSSDILNIQQAIGATQNQ
4swissprot_carp_crypa     TSTGYAVGS--GTFKSTSIDGIADTGTTLLYLPATVVSAYWAQVSGAKSS
                             .   . :..  ..          ****. :  *::             ..

1swissprot_carp_rhimi     TQQ-GWVVPCASYQNSKSTISIVMQKSGS--SSDTIEISVPVSKMLLPVD
2swissprot_carp_rhipu     SQQ-GYTVPCSKYQDSKTTFSLVLQKSGS--SSDTIDVSVPISKMLLPVD
3swissprot_chym_bovin     YG--EFDIDCDNLSYMPTVVFEINGKMYP--LTPSAYTSQDQGFCTSGFQ
4swissprot_carp_crypa     SSVGGYVFPCSATLPSFTFGVGSARIVIPGDYIDFGPISTGSSSCGGGIQ
                             :  . *          :             .        *   .    . :

1swissprot_carp_rhimi     QSNETCMFIILPDGGNQYIVGNLFLRFFVNVYDFGNNRIGFAPLASAYEN
2swissprot_carp_rhipu     KSGETCMFIVLPDGGNQFIVGNLFLRFFVNVYDFGKNRIGFAPLASGYEN
3swissprot_chym_bovin     SENHSQKWILGDVFIREYYSVFDRANNLVGLAKAI---------------
4swissprot_carp_crypa     SSAGIGINIFGDVALKAAFVVFNGATTPTLGFASK---------------
                             ..           *.      .           .

1swissprot_carp_rhimi     E
2swissprot_carp_rhipu     N
3swissprot_chym_bovin     -
4swissprot_carp_crypa     -
```

Table 1: Amino acid sequence comparison of four coagulants using the Clustal W method. Proteins are numbered as indicated in the text. Identical residues are indicated with an asterisk, homologous residues with double or single points. Catalytic Aspartic residues are highlighted in dark. Residues that are not conserved in pepsins, gastricsin and cathepsin, but are conserved in the coagulants, are highlighted in grey.

Since conservation of the primary amino acid sequence is so low among the different coagulants, no single amino acids or domains can be pin-pointed that might explain the difference in quality in the cheese making process. However, we found that it is possible to distinguish the coagulants from other aspartic proteases, like pepsin, gastricsin and cathepsin.

Therefore, the 42 amino acids that are conserved between the coagulants were checked for their presence in other aspartic proteases. Since most of these amino acids are part of the catalytic centre of all aspartic proteases, only 6 are not conserved; Thr28, Asp43, Ile80, Ala136, Asn157 and Ser299 (numbering according to the *Rhizomucor miehei* sequence in the Protein Data Bank (PDB) accession number 2ASI). These 6 residues are highlighted in grey in Table 1.

When these 6 amino acid residues are displayed on the tertiary structure of the R. miehei aspartic protease, Ala136, Asp43 and Ile80 seem to be in the vicinity of the catalytic residues and the binding pocket of the enzyme, and hence might have influence on the substrate specificity of the enzyme.

Of these 6 residues only Asp43 seems to be specific for the coagulants. This residue is always an Asn in pepsins, gastricins and cathepsins. Therefore, Asp43 might be specific for the quality of the coagulants in the cheese making process.

Using the specificity of Asp43 for coagulants, a consensus motif is specified. In the primary sequence of the coagulants, Asp43 is in the immediate vicinity of the conserved residues around the catalytic residue Asp38. Therefore, a consensus sequence was defined and tested for specificity by a databank search.

The consensus amino acid sequences for coagulants are: FDTGSSD or FDTGSSE (SEQ ID NO: 4 or SEQ ID NO: 5).

A search for this motif in several DNA- and protein-databases yielded the following genes:

Chymosins
chymosin—Ovis ammon aries (domestic sheep)
chymosin—Bos taurus (calf)
chymosin—Bos primigenius (aurochs)
chymosin—Bubalus amee bubalis (water buffalo)
chymosin—Callithrix jacchus (white-tufted-ear marmoset)
chymosin—Camelus dromedarius (arabian camel)
chymosin—Sus scrofa (pig)
chymosin—Rattus norvegicus (rat)

PAGs
pregnancy-associated glycoprotein—approximately 35 entries

Further Animal
aspartic protease—Trematomus bernacchii (fish)
aspartic proteinase—"nothepsin"—Danio rerio (zebrafish)
cathepsin—Chionodraco hamatus (fish)
aspartyl protease NM1—Bovine
Drosophila melanogaster genomic scaffold 142000013386055 section 23 of 63
Drosophila melanogaster genomic scaffold 142000013386046 section 5 of 16

Fungal
mucorpepsin—Rhizomucor pusillus
mucorpepsin—Rhizomucor miehei
endothiapepsin—Cryphonectria parasitica (chestnut blight fungus)
syncephapepsin—Syncephalastrum racemosum
aspartic protease—Glomerella cingulata
aspartic protease—Botryotinia fuckeliana
aspartic protease—Fusarium oxysporum
aspartic protease—Amanita muscaria (fly agaric)
aspartic protease SAP1—Rhizopus oryzae
aspartic protease SAP2—Rhizopus oryzae
rhizopuspepsin I—Rhizopus chinensis
rhizopuspepsin II—Rhizopus chinensis
rhizopuspepsin II—Rhizopus niveus
rhizopuspepsin III—Rhizopus niveus
rhizopuspepsin V—Rhizopus niveus Plant
preprocardosin B—Cynara cardunculus
hypothetical protein F4D11.90—Arabidopsis thaliana
AT4g32710; product: "putative protein kinase"; Arabidopsis thaliana Screening for this motif yielded relatively few hits, of which many were enzymes that could potentially function in coagulation.

Not only public libraries can be screened. The person skilled in the art will appreciate that non-sequenced genomes of micro-organisms can also be screened using this end if for rennet useful in cheese making processes. Fungi, especially those which are food-grade, can be screened. For example fungi from the class Eurotiomycetes. Within these class the genera Aspergillus and Penicillium are preferred.

The present invention also discloses a novel enzyme which is of fungal origin whereby the fungal origin is of the class Eurotiomycetes and has the consensus motif. Preferably, this fungus is of the order Eurotiales, more preferably of the family Trichocomaceae, even more preferably of the genus Aspergillus or Penicillium and is for example an Aspergillus niger or Aspergillus oryzae rennet having the motif. Preferably, the rennet is encoded by a gene comprising the sequence as depicted in SEQ ID NO: 1 or SEQ ID NO: 2. The preferred protein is depicted in SEQ ID NO: 3.

As described above, the present invention provides methods to identify enzymes which are encoded by a DNA sequence comprising the consensus amino acid sequence (FDTGSSD or FDTGSSE; SEQ ID NO: 4 or 5).

According to an embodiment of the invention the identified enzymes can be produced on industrial scale. In the case of enzymes from a micro-organism, the micro-organism producing the identified enzyme can be cultured and the identified enzyme can be recovered from the fermentation broth or from the micro-organism. According to another embodiment of the invention, the DNA coding for the identified enzymes is cloned using cloning techniques known in the art and the cloned DNA is expressed in a suitable host cell. In a preferred embodiment the aspartic protease from Aspergillus niger is overexpressed in an Aspergillus host cell, preferably an Aspergillus niger host cell.

The aspartic protease of the invention is advantageously used for the industrial production of food and feed. Preferably, the aspartic protease is used for the production of cheese. The present invention therefore provides the use of an aspartic protease of fungal origin in cheese production whereby the fungal origin is from the class Eurotiomycetes and the aspartic protease is encoded by a DNA sequence comprising the consensus amino acid sequence (FDTGSSD or FDTGSSE; SEQ ID NO: 4 or 5). Preferably the fungal origin is of the order Eurotiales, more preferably of the family Trichocomaceae and even more preferably of the genus Aspergillus, Penicillium or Talaromyces. An example of such an aspartic protease Talaromyces emersonii is given in Database EMBL 'online', 13 Dec. 2001, O'DONOGHUE et al. "Talaromyces emersonii pepsin-type protease gene, partial cds." Database accession no. AF439995 XP 002213596.

LEGEND TO THE FIGURES

FIG. 2: SDS-polyacrylamide gel stained with Coomassie Brilliant Blue. Culture filtrate of transformants 15.2, 15.3 and CBS513.88 (wt) were treated for 24 hours in the presence (+) or absence (−) of endoH before loading the gel. The glycosylated and de-glycosylated form of the rennet, produced in the transformants, is represented by arrows

EXAMPLES

Example 1

Identification of a Rennet from *Aspergillus niger*

The sequenced genome of *Aspergillus niger* contains many genes encoding aspartic proteases. However it was unclear if any a specific aspartic protease would be useful as rennet in cheese making applications. Here we propose that aspartic proteases containing the peptide motif FDTGSSD/E (SEQ ID NO: 4/5) would be preferably suitable for the use in milk coagulation and cheese ripening.

Using the peptide motif FDTGSSD/E (SEQ ID NO: 4/5) the sequenced and annotated genome of *Aspergillus niger*-CBS513.88 was screened for the presence of a gene encoding an aspartic protease that might be suitable as rennet in cheese production.

Of the many genes encoding aspartic proteases in the *Aspergillus niger* genome, only one gene was identified using the screening with the rennet motif described above. The DNA sequence of this gene is depicted in SEQ ID NO:1. The open reading frame, deduced from the DNA sequence is depicted in SEQ ID NO:2, and the protein sequence deduced from the open reading frame is depicted in SEQ ID NO: 3.

Example 2

Identification of Rennets in Other Species

A person skilled in the art will appreciate that the present invention can be applied to the identification of rennets from other species. Most convenient, a computer aided search of the DNA-and/or protein-databases is performed. For this specific purpose useful programs are available in the public domain. The internet site http: double slash www dot ncbi dot nim dot nih dot gov slash blast slash Blast dot cgi provides the possibility of searching public domain DNA- and/or protein-sequences using the BLAST programs. A search was done using the BLASTP2.2.1 program, a wordsize of 3, no filter, the BLOSUM62 matrix, gapcosts-existence of 11, and extension 1. The peptide motif FDTGSSD (SEQ ID NO: 4) was used, and a comparison was done with the non-redundant Genbank CDS translations+PDB+Swissprot+PIR+PRF sequence databases, of Oct. 1, 2001. Obviously a similar search can be performed with the motif FDTGSSE (SEQ ID NO: 5). For a search in such a large database it is relevant to put the expect threshold at 15,000. When searches are performed in other databases of different size, the expect threshold should be adjusted accordingly. An extensive manual for sequence similarity searches is available at the same internet site.

Both searches combined yielded 83 exact hits in the database, which included the protein sequences of all currently known commercial rennets, all known chymosins from various organisms and several aspartic proteases from fungi. However, animal pepsins and cathepsins were hardly represented in the dataset, indicating that the motif is highly discriminative for aspartic proteases having coagulant properties. Since the databases contain more then 40,000 sequences coding for proteolytic enzymes, the use of the FDTGSSD/E (SEQ ID NO: 4/5) motif is a powerful tool to distinguish between aspartic proteases with rennet activity and the majority of the proteases which lack this activity.

Obviously, the genes coding for aspartic proteases with rennet function identified using this method can be cloned and overexpressed in a suitable expression host. Preferably, the gene encoding an aspartic protease is originating from a fungus and overexpressed in *Aspergillus niger* to obtain high quantities of the rennet for industrial application.

Example 3

Isolation of Genes Encoding Rennets, When the DNA Sequence is Unknown.

Using this peptide sequence motif, it is also possible to isolate genes encoding rennets when the gene sequence is unknown. Methods have been described in literature to design degenerate oligonucleotide primers that can be used for this purpose (Sambrook et al. (1989) Molecular cloning: a laboratory manual. Cold Spring Harbor Laboratory Press). Also, methods to isolate genes from an organism, using a degenerate oligonucleotide as probe or primer, have been described.

Oligonucleotides that code for the peptide motif FDTGSSD/E are useful for isolation of the genes encoding aspartic proteases with rennet properties will. The sequences of these oligonucleotides is 5'-TTYGAYACNGGNTCNTC-NGA-3', 5'-TTYGAYACNGGNTCNAGYGA-3', 5'-TTYGAYACNGGNAGYTCNGA-3' or 5'-TTYGAYAC-NGGNAGYAGYGA-3' where Y=T or C and N=A or G or T or C (SEQ ID NO's: 6-9). Other useful oligonucleotides for screening for genes encoding rennets, are the complement and reverse of the first oligonucleotides; 5'-TCNGANGA-NCCNGTRTCRAA-3', 5'-TCRCTNGANCCNGTRT-CRAA-3', 5'-TCNGARCTNCCNGTRTCRAA-3' or 5'-TCRCTRCTNCCNGTRTCRAA-3' where R=A or G and N=A or G or T or C (SEQ ID NO's:10-13).

The degeneracy of such a group of oligonucleotides may be decreased by the introduction of inosine (I) bases at the. N positions. Additionally, Y may be replaced by T, and R may be replaced by G, in order to decrease degeneracy with only a small effect on specificity. Furthermore, for screening the presence of genes encoding rennets in organisms of which the codon preference is known, the degeneracy of the oligonucleotide can be further decreased by taking the codon preference into account in the design of the oligonucleotide. A person skilled in the art will know how to do this. Furthermore, all possible combinations of oligonucleotide primers, without degeneracy, may be synthesized separately and used in individual screening experiments.

First, a genomic, cDNA or EST library is constructed from the species of interest in a universal vector. Suitable methods for library construction are described in literature (Sambrook et al. (1989) Molecular cloning: a laboratory manual. Cold Spring Harbor Laboratory Press). Second, a degenerate oligonucleotide described above is used in a PCR reaction together with one universal oligonucleotide that primes in the vector, at the border of the recombinant DNA insert, on DNA isolated from the library. Useful strategies have been described in literature for the isolation of a desired gene when only a single degenerate oligonucleotide primer is available (e.g. Minambres et al. (2000) Biochem. Biophys. Res. Commun. 272, 477-479; PCR technology (1989) Ed. H. A. Erlich pp. 99-104, Stockton Press). Third, the PCR amplified fragment is then labelled and used as probe for the screening of the library by conventional means. The full length gene can than be subcloned into an expression vector suitable for overexpression of the rennet in a desired production host organism.

In a different approach, when no library is available from the species that is screened for the presence of a gene encoding a rennet, part of the gene can be amplified by 3'-RACE. For this, RNA is isolated from the species of interest and used in a 3'-RACE reaction using primer 1 (SEQ ID NO's: 6-10) as gene specific primer. The amplification of part of an unknown cDNA using one degenerate oligonucleotide and one universal primer, by 3'-RACE, has been described previously (WO99/38956).

The traditional method to isolate a full-length gene using the information from only a small peptide, is hybridization of a labelled degenerate oligonucleotide to filters on which a library is replicated. Methods describing the screening of gene libraries using degenerate oligonucleotides, and methods to calculate or determine the optimal hybridization conditions of these oligonucleotides, have been extensively described in literature (Sambrook et al. (1989)). The oligonucleotides described above may be used for this method to isolate genes encoding a rennet from different species.

In a variation to this method, a partial gene library can be constructed first. For this, DNA is fractionated, after which fragments of DNA containing the gene coding for a rennet are detected by hybridization to the labelled oligonucleotides described above. These fragments are isolated and used in the construction of a partial gene library enriched in the gene coding for a rennet. This library can than be screened by conventional means. For this method, genomic DNA is first digested with restriction enzymes before fractionation by gel-electrophoresis, while cDNA can be fractionated directly.

A different method to isolate the gene coding for a rennet is by using antibodies raised against the peptide FDTGSSD/E (SEQ ID NO: 4/5). Antibodies may be monoclonal or polyclonal. Methods describing the production of antibodies specific for small peptides have been extensively described in literature (Harlow, E and Lane, D (1988) Antibodies; a laboratory manual, ISBN 0-87969-314. -2).

Expression libraries can be constructed from the species of interest, by cloning cDNA or genomic DNA into a vector suitable for expressing the insert in a convenient host, such as E. coli or yeast. Expression vectors may or may not be based on phage lambda. Immunodetection of antigens produced by expression libraries, and methods describing the purification of specific clones expressing the antigen have been published. Using an antibody specific for the peptide sequence motif FDTGSSD/E (SEQ ID NO: 4/5), it is possible to isolate the gene encoding the rennet encompassing this motif, using this method.

In effect, many different method may be used to isolate a gene coding for a rennet when the information described in this invention is taken into account. The advantage of using the FDTGSSD/E (SEQ ID NO: 4/5) peptide sequence information over prior art methods, is the speed and relative ease with which a new gene coding for a rennet can be identified. The use of sequence information gives an indication of the value of a new aspartic protease in cheese making, without performing laborious testing of all aspartic proteases in direct application experiments.

Example 4

Cloning and Overexpression of a Rennet from *Aspergillus niger*

Figure 1:
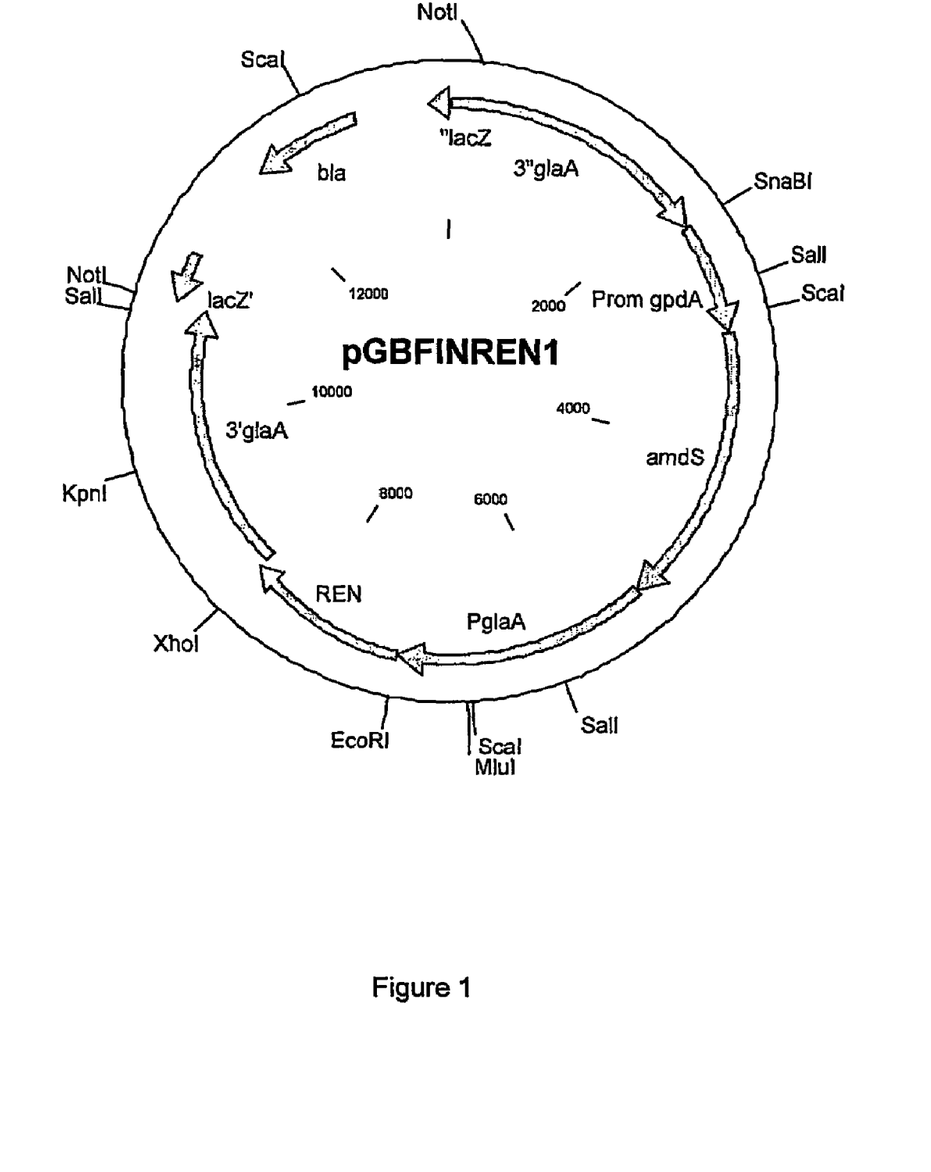
FIG. 1: Schematic map of expression plasmid pGBFIN-REN1 where the rennet coding sequence is cloned downstream of the A. niger glaA promoter. Direct selection for transformants can be done for the presence of the A. nidulans amdS gene, which is present on the plasmid downstream of the gpdA promoter. Directed genomic integration will occur via the 3' and 3"-glaA flanking sequences in *A. niger.*
Figure 2:
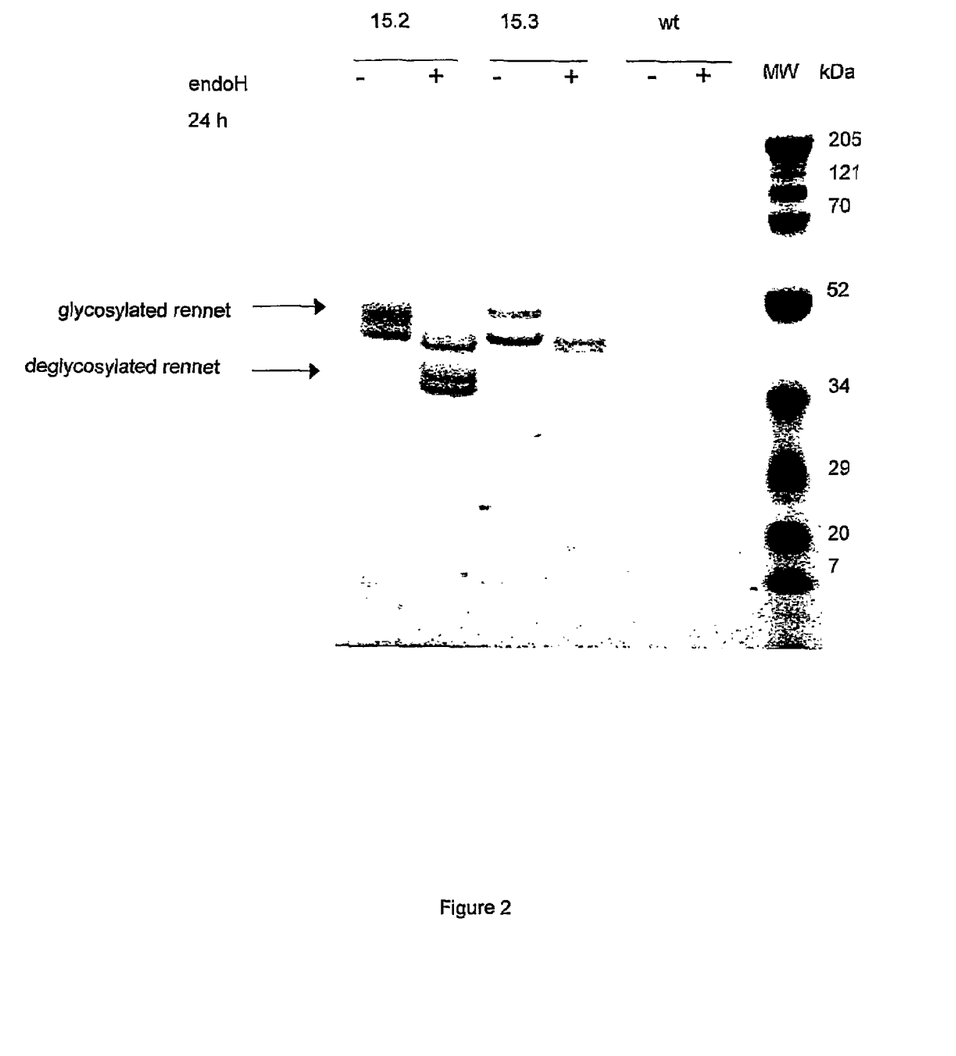

General molecular biological methods were performed as described in Sambrook et al. (1989). To verify that the protein sequence of SEQ ID NO: 3 is an aspartic protease with the special property that it can be used as a coagulant in cheesemaking, the coding sequence was cloned and brought to overexpression in *Aspergillus niger*. For this, oligonucleotide primers 5'-GTACTGGAATTCATGCAGCTC CTCCAGTC-CCTC-3' (SEQ ID NO: 18) and 5'-GTACTGGAATTC-CTAGTTCTTGGGAG AGGCAAC-3' (SEQ ID NO: 19) were synthesized and used in PCR amplification of the coding sequence of the putative rennet from *Aspergillus niger* CBS513.88 using conventional techniques. The amplified PCR fragment was cloned in the *A. niger* expression vector pGBFIN-11 (WO9932617) by digestion of both the fragment and the vector with EcoRI and ligation. After amplification in *E. coli* the correct expression plasmid was selected, and is named pGBFINREN1 (FIG. 1). Isolated plasmid DNA of pGBFINREN1 was digested with NotI, which removes all *E. coli* derived sequences from the expression vector, purified by agarose gel extraction, and transformed to *Aspergillus niger* CBS513.88 essentially using techniques described before (WO9846772). It is also described how to select for transformants on agar plates containing acetamide, and to select targeted multicopy integrants. Several isolated transformants were tested for production of the putative rennet by inoculation in liquid medium and cultivation. A useful method for cultivation of *A. niger* strains and separation of the mycelium from the culture broth is described in WO9846772. Growth was for several days at 34 degrees Celsius by shaking at 200 rpm. Samples of the culture filtrate of transformants 15.2 (high copy transformant) and 15.3 (low copy transformant) were taken and analysed by SDS-polyacrylamide gel-electrophoresis. A stained gel showing the production of rennet protein in these strains is shown in FIG. 2. The presence of rennet in the culture filtrate shows that this enzyme is secreted from *A. niger*. Treatment of the samples with endoglycosidase-H (Endo H; Sigma) before loading the gel reveals that the protein is heavily glycosylated when grown under these conditions. Production of the rennet is proportional to the gene copy number in the different transformants.

Example 5

Analysis of the Biochemical Properties of the Aspergillus niger Rennet

A. niger transformant 15.2 was grown for 6 days at 34 degrees C. in 10 liter of a synthetic medium. After filtration the liquid obtained was concentrated by ultrafiltration and then purified by chromatography over a HIC column (butyl Sepharose 4FF; Amersham Pharmacia). Although the A. niger rennet did not bind to this resin, all contaminating proteins were effectively removed. Residual low molecular weight components were removed in a subsequent ultrafiltration step.

In a first test the purified A. niger rennet was incubated with a number of different protease inhibitors (Sigma). The relatively strong effect of pepstatin suggests that the A. niger rennet is an aspartic endoprotease just as well known milk clotting enzymes like calf chymosin (EC3.4.23.4) and Mucor rennin (EC3.4.23.23). Upon its addition to milk the A. niger rennet initiated a clotting reaction which is visually similar to the clotting reaction initiated by calf chymosin and Mucor rennin. Unlike combinations of milk with so called broad spectrum proteases, prolonged incubation (during 16 hours) with the A. niger rennet does not lead to a resolubilization of the clotted milk.

Calf chymosin and Mucor rennin are also known to cleave the synthetic substrate H—Leu—Ser—p—nitro—Phe—Nle—Ala—Leu—OMe (Bachem, Switzerland) very specifically (Martin et al.; Biochem. Biophys. Acta 612, 410(1980)). The A. niger rennet cleaved also very specifically. Tests carried out on this substrate at different temperatures and different pH values indicated a pH optimum around 5 and a temperature optimum of approx 50 degrees C. for the new A. niger enzyme. Using the same approach the activity of a cloned calf chymosine (Maxiren® 600, DSM Food Specialities, The Netherlands) and the A. niger protease were compared at 30° C. at different pH values. Compared with chymosine the pH optimum of the A. niger protease turned out to be only marginally higher (pH 4.8-5.0 vs. 4.0-4.3).

Finally the temperature stability of the A. niger rennet was determined using the above mentioned synthetic peptide. After an incubation for 30 minutes at pH 5.0 and 50 degrees C. approx 70% of the initial activity survived.

Example 6

Use of the Aspergillus Rennet in Cheese Making

Miniature cheeses were manufactured according to Shakeel-Ur-Rehman et al. (Lait, 1998,607-620). Standard centrifuge bottles (250 mL) served as cheese vats. Each miniature cheese resulted from 200 mL pasteurised, unstandardised full fat milk (pasteurisation at 63° C. for 30 minutes). All additions (starter culture, CaCl2 and rennet), as well as the various processing steps, were made directly into these cheese vats. The starter culture used was DELVO-TEC® LL50D (DSM Food Specialties, Delft, the Netherlands). Two batches, of 4 cheeses each, were manufactured with Maxiren® 600 (chymosine) and Fromase® 750XL (Mucor rennet, DSM Food Specialties, Delft, The Netherlands) as control rennets and our novel A. niger rennet-like enzyme in duplicate in both batches. Every miniature cheese had 8 IMCU (International Milk Clotting Units, IDF Standard 110A, Appendix A, 1987) added, to allow for an even comparison. Given the variation in IMCU's of the different rennets, a protein determination (Macro Kjeldahl method) was made and the protein content of the volume of enzyme used was accounted for in the final mass balance to allow for a fair comparison of the yields obtained. The coagulum was cut following 45 minutes of renneting. Behaviour of the individual rennet enzymes during coagulation of the milk was of a visual nature. The curd/whey mixture was separated using a centrifuge (5,000 g for 1 hour) when the pH of the mixture reached 6.2. A swing-out rotor was used. When the pH of the curd reached 5.2-5.3, a second centrifuge step was done to allow for some more whey to be expelled (20 minutes at 5,000 g). The cheeses were brined for 30 minutes inside the centrifuge bottles using a 20% NaCl, 0.05% CaCl2 brine. At this stage a mass balance (weight in and out) was determined of each individual miniature cheese.

TABLE 1

Mass balance results of miniature cheese manufacture.

| Batch number | Maxiren ® 600 | | | Fromase ® 750XL | | | A. niger rennet | | |
|---|---|---|---|---|---|---|---|---|---|
| | weight milk | weight curd | ratio curd/milk | weight milk | weight curd | ratio curd/milk | weight milk | weight curd | ratio curd/milk |
| 1 | 210.02 | 27.24 | 12.97 | 211.07 | 26.89 | 12.74 | 210.22 | 27.81 | 13.23 |
| | | | | | | | 208.69 | 27.62 | 13.24 |
| 2 | 208.30 | 28.53 | 13.70 | 207.50 | 27.76 | 13.38 | 208.97 | 29.30 | 14.02 |
| | | | | | | | 209.33 | 29.31 | 14.00 |

Visual observations showed our novel A. niger rennet-like enzyme causing a slightly firmer coagulum than the two other rennets. According to the mass balances obtained the curd to milk ratio of the *A. niger* rennet-like is in the same league as for both other renneting enzymes.

---

The invention claimed is:

1. An isolated aspartic protease comprising the amino acid sequence of SEQ ID NO: 3.

2. A method to prepare food or feed using the aspartic protease of claim 1 which method comprises contacting a food or feed preparation with the aspartic protease.

3. The method of claim 2 wherein cheese is prepared.

4. The method of claim 2 wherein milk is clotted or coagulated.

5. A process for identifying milk clotting enzymes comprising screening amino acid sequences for the presence of FDTGSSD or FDTGSSE (SEQ ID NO: 4 or 5).

6. The process of claim 5 wherein:
 (a) the amino acid sequences originate from a public library or a microorganism, plant or animal; or
 (b) the amino acid sequences are encoded by sequences originating from a public library or a genome of the microorganism, plant or animal.

* * * * *